United States Patent [19]

Uekusa et al.

[11] Patent Number: 4,882,544
[45] Date of Patent: Nov. 21, 1989

[54] SIMPLE INSPECTION DEVICE FOR ANALYZER FOR IONIC ACTIVITY MEASURMENT

[75] Inventors: Tadashi Uekusa; Takashi Koizumi; Nobuhiko Amano, all of Kanagawa, Japan

[73] Assignee: Fuji Photo Film Co., Ltd., Kanagawa, Japan

[21] Appl. No.: 287,379

[22] Filed: Dec. 21, 1988

Related U.S. Application Data

[63] Continuation of Ser. No. 106,467, Oct. 9, 1987.

[30] Foreign Application Priority Data

Oct. 9, 1986 [JP] Japan .................................. 61-241010
Apr. 17, 1987 [JP] Japan .................................. 62-94551

[51] Int. Cl.⁴ ............................................ G01R 31/02
[52] U.S. Cl. ..................................... 324/511; 204/401
[58] Field of Search ....................... 204/401, 407, 416; 73/1 R; 324/63, 74, 511, 555

[56] References Cited

U.S. PATENT DOCUMENTS 4,053,381 10/1977 Hamblen et al. ..................... 204/416
4,797,193 1/1989 Uekusa et al. ........................ 204/416

Primary Examiner—G. L. Kaplan
Attorney, Agent, or Firm—Sughrue, Mion, Zinn, Macpeak & Seas

[57] ABSTRACT

A simple inspection device is constituted for inspection of an analyzer for measuring ionic activity by using an ionic activity measuring device provided with at least one ion selective electrode pair for generating potential corresponding to ionic activity fo a predetermined ion, and a porous bridge for associating the electrodes of the ion selective electrode pair with each other, and by contacting potential difference measuring probes respectively with the electrodes of the ion selective electrode pair, thereby to measure a difference in potential between the electrodes. The simple inspection device comprises a supporting member having outer dimensions approximately equal to ther outer dimensions of the ionic activity measuring device, and an electrically conductive member supported on the supporting member for short-circuiting across the potential difference measuring probes when the potential difference measuring probes are contacted with the electrically conductive member.

5 Claims, 6 Drawing Sheets

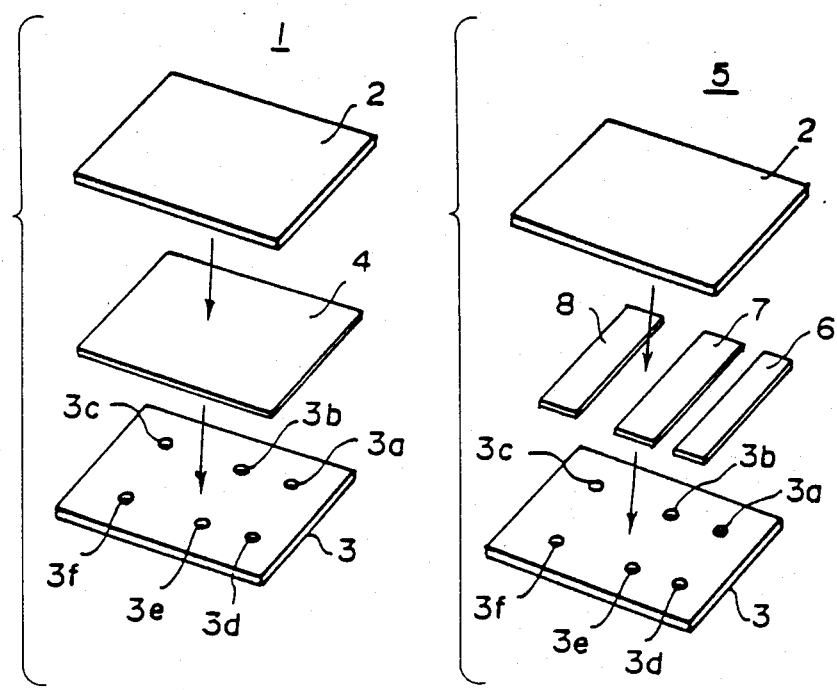

FIG.10
FIG.11
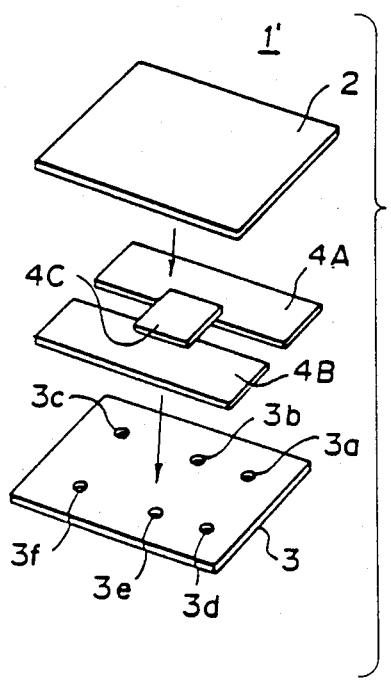
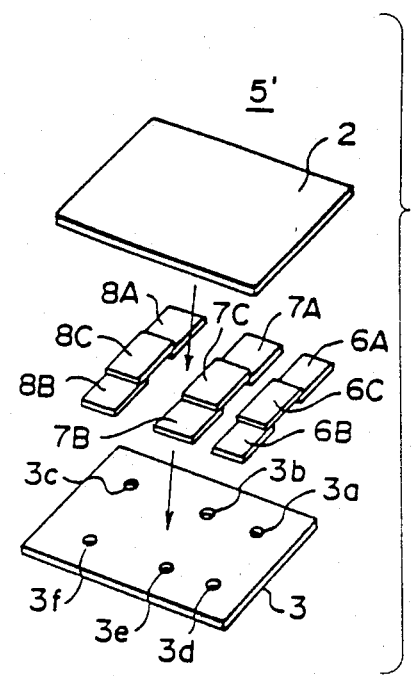

SIMPLE INSPECTION DEVICE FOR ANALYZER FOR IONIC ACTIVITY MEASURMENT

This is a continuation of application Ser. No. 106,467 filed 10.9.87.

BACKGROUND OF THE INVENTION

Field of the Invention

This invention relates to a device for inspecting the functions of an analyzer used for quantitatively analyzing the activity or concentration of a specific ion contained in an aqueous liquid sample, for example, a liquor, a beverage, service water, and in particular a body fluid (blood, urine, saliva or the like), by potentiometry using a slide type ionic activity measuring device.

Description of the Prior Art

As disclosed in, for example, Japanese Patent Publication No. 58(1983)-4981, and Japanese Unexamined Patent Publication Nos. 58(1983)-156848 and 58(1983)-211648, there has been proposed a slide type ionic activity measuring device for receiving a liquid sample fed in drops and measuring the activity of a specific ion contained in the sample.

The slide type ionic activity measuring device (hereinafter often referred to as a slide) comprises at least one ion selective electrode pair consisting of ion selective electrodes generating a potential corresponding to the ionic activity of a predetermined ion, and a porous bridge disposed for communication between the electrodes of the ion selective electrode pair. A reference solution containing a predetermined ion whose ionic activity is known is applied to one of the electrodes of the ion selective electrode pair, and sample solution whose ionic activity is unknown is applied to the other of the ion selective electrode pair. By the effect of the porous bridge, the reference solution and the sample solution contact each other to achieve a liquid-junction, thus electrical conduction, therebetween. As a result, a difference in potential corresponding to the difference in ionic activity between the reference solution and the sample solution arises between the electrodes of the ion selective electrode pair. By measurement of the difference in potential, the activity of the specific ion contained in the sample solution can be determined on the basis of a calibration curve determined in advance (by use of the Nernst equation).

In order to measure the ionic activity by use of the aforesaid slide type ionic activity measuring device, an analyzer which applies a reference solution and a sample solution and measures a difference in potential should preferably be used. Such an analyzer is described in, for example, U.S. Pat. No. 4,257,862 and Japanese Patent Application No. 59(1984)-12794. The conventional analyzer of this type is constituted to send the slide type ionic activity measuring device to a potential measuring section after the application of the reference solution and the sample solution, and to contact potential measuring probes respectively with the electrodes of the aforesaid electrode pair at the potential measuring section, to thereby measure the difference in potential between the electrodes.

In the course of manufacture and usage of the analyzer having the arrangement as mentioned above, it is necessary to inspect whether the analyzer is or is not capable of operating normally. Specifically, for example, the manufacturer must carry out a delivery inspection and other inspections, and the serviceman and the user must inspect the analyzer for maintenance and confirmation of measured values.

As in the case of various other measuring apparatuses, the aforesaid inspection can be achieved electrically by use of a tester or the like.

However, it is troublesome to use a tester or the like for the aforesaid inspection. Also, in some cases, the serviceman or the user must carry the tester or the like with him. In such cases, it is even more troublesome to carry out the inspection by use of the tester or the like.

SUMMARY OF THE INVENTION

The primary object of the present invention is to provide a simple inspection device for a simple determination of whether an analyzer for ionic activity measurement is or is not capable of operating normally.

Another object of the present invention is to provide a simple inspection device for an analyzer for ionic activity measurement, Which is suitable for carrying out inspections of the analyzer simply and efficiently in the course of manufacture, maintenance and usage of the analyzer.

The present invention provides a simple inspection device for an analyzer for ionic activity measurement, which is used for inspecting the functions of the analyzer for measuring ionic activity by using an ionic activity measuring device provided with at least one ion selective electrode pair for generating an electric potential corresponding to ionic activity of a specific ion, and a porous bridge disposed to associate the electrodes of the ion selective electrode pair with each other, and by contacting potential difference measuring probes respectively with the electrodes of the ion selective electrode pair, to thereby measure a difference in potential between the electrodes, the simple inspection device for an analyzer for ionic activity measurement comprising:

(i) a supporting member having outer dimensions approximately equal to the outer dimensions of said ionic activity measuring device, and (ii) an electrically conductive member supported on said supporting member for short-circuiting across said potential difference measuring probes when said potential difference measuring probes are contacted with said electrically conductive member.

The present invention also provides a simple inspection device for an analyzer for ionic activity measurement, wherein instead of the aforesaid electrically conductive member, a pair of good electrical conductors of high conductivity are disposed at positions for contact with the potential difference measuring probes, and a chip resistor for associating said electrical conductors with each other and having an electrical resistance approximately equal to the electrical resistance produced across the electrodes of the ion selective electrode pair at the time electrical conduction is achieved between said electrodes by the porous bridge through which a sample solution and a reference solution have spread are supported on the supporting member.

The first-mentioned simple inspection device for an analyzer for ionic activity measurement in accordance with the present invention, wherein the supporting member has outer dimensions approximately equal to the outer dimensions of the ionic activity measuring device, can be set at a potential difference measuring section of the analyzer in the same manner as the slide. After the first-mentioned simple inspection device is set at the potential difference measuring section, the potential difference measuring probes are moved in the same manner as in the course of measurement of a difference in potential, and are contacted with the electrically conductive member of the simple inspection device, to thereby short-circuit across the probes. As a result, the difference in potential between the probes is found to be zero if the analyzer is normal. On the other hand, the difference in potential between the probes does not become zero if the analyzer is not normal, for example, if a contact failure portion, a broken wire, a defective relay, a defective amplifier or the like is present in the electric circuit of the analyzer. Therefore, abnormal conditions of the analyzer can be found.

With the second-mentioned simple inspection device in accordance with the present invention, then abnormal condition of the analyzer can be found in the same manner as mentioned above. However, in this case, a ground failure of the electric circuit or the main body of the analyzer can also be found. Specifically, in the case where a ground failure arises within the electric circuit of the analyzer, the aforesaid potential is caused to fluctuate unstably to the "+" (plus) side or to the "−" (minus) side by adverse effects of noise upon the electric circuit. Therefore, the ground failure can be found by investigating the fluctuation of the potential. On the other hand, in the case where the first-mentioned simple inspection device is used, the electric circuit is not adversely affected by noise even though a ground failure arises, and therefore the ground failure cannot be found as with the second-mentioned simple inspection device.

In the simple inspection device for an analyzer for ionic activity measurement in accordance with the present invention, the electrically conductive member for short-circuiting across the probes when the probes are contacted with the electrically conductive member, or the high conductivity electrical conductors and the chip resistor for achieving electrical conduction across the probes via an electrical resistance approximately equal to the electrical resistance produced across the electrodes of the ion selective electrode pair in the course of the usage of the ionic activity measuring device are supported on the supporting member which can be processed in the same manner as the ionic activity measuring device. Therefore, with the simple inspection device for an analyzer for ionic activity measurement in accordance with the present invention, it is possible to determine very simply whether the analyzer for ionic activity measurement is or is not operating normally. Accordingly, the inspection work by the manufacturer, the serviceman or the user of the analyzer can be achieved very simply and efficiently.

BRIEF DESCRIPTION OF THE DRAWINGS

FIGS. 8 and 9 are perspective exploded views showing embodiments of the first simple inspection device for an analyzer for ionic activity measurement in accordance with the present invention, and FIGS. 10 and 11 are perspective exploded views showing embodiments of the second simple inspection device for an analyzer for ionic activity measurement in accordance with the present invention.

DESCRIPTION OF THE PREFERRED EMBODIMENTS

The present invention will hereinbelow be described in further detail with reference to the accompanying drawings.

Figure 1:
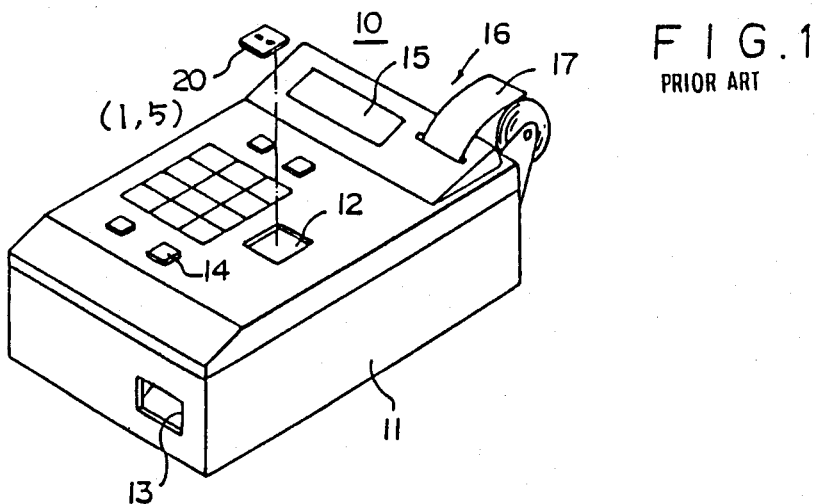
FIG. 1 is a perspective view showing an example of an analyzer for ionic activity measurement to which the simple inspection device in accordance with the present invention is applied.

First, an analyzer for ionic activity measurement, to which the simple inspection device in accordance with the present invention is applied, and a slide type ionic activity measuring device used in the analyzer will be described below. Referring to FIG. 1, outer surfaces of an analyzer 10 are covered with a cover 11. The cover 11 has an opening 12 for receiving a slide type ionic activity measuring device (slide) 20 and allowing application of a reference solution and a sample solution to the slide 20, and an ejection opening 13 for ejecting the slide 20 after potential difference measurement is finished. The analyzer 10 is provided with a start pushbutton 14, an ionic activity displaying section 15, and an ionic activity recording section 16.

Figure 2:
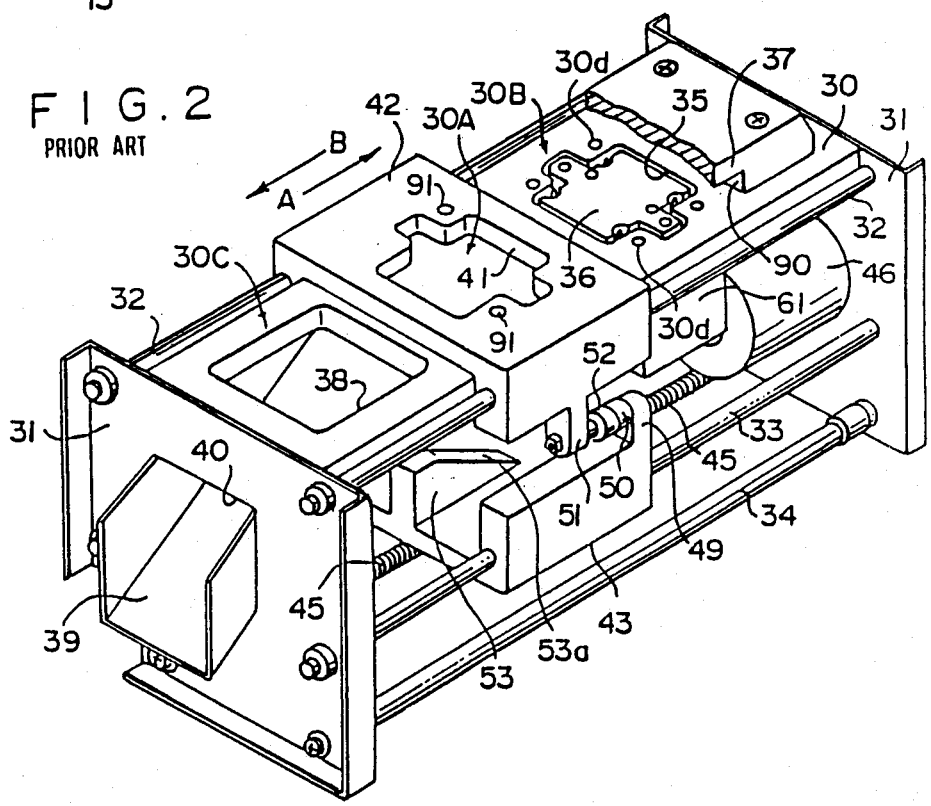
FIGS. 2, 3 and 4 are respectively a perspective view, a plan view, and a sectional side view showing a major part of the analyzer shown in FIG. 1.
Figure 3:
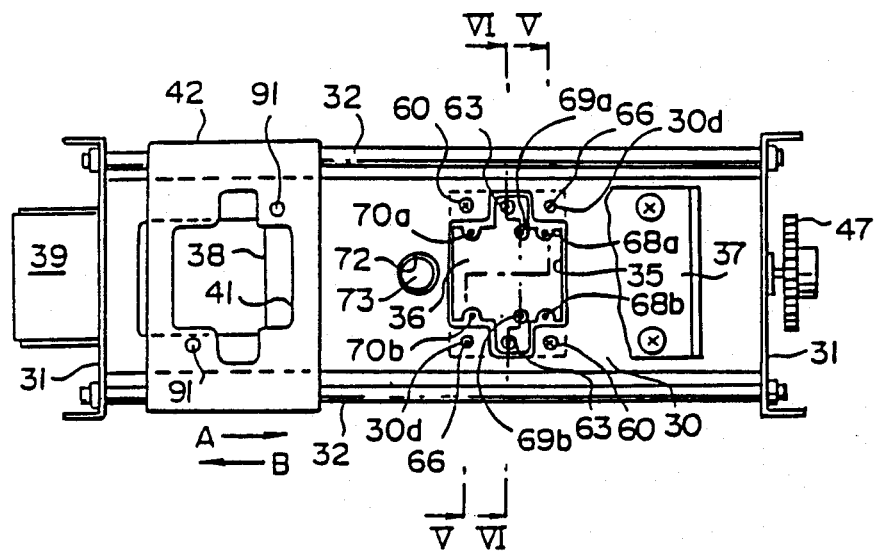
Figure 4:
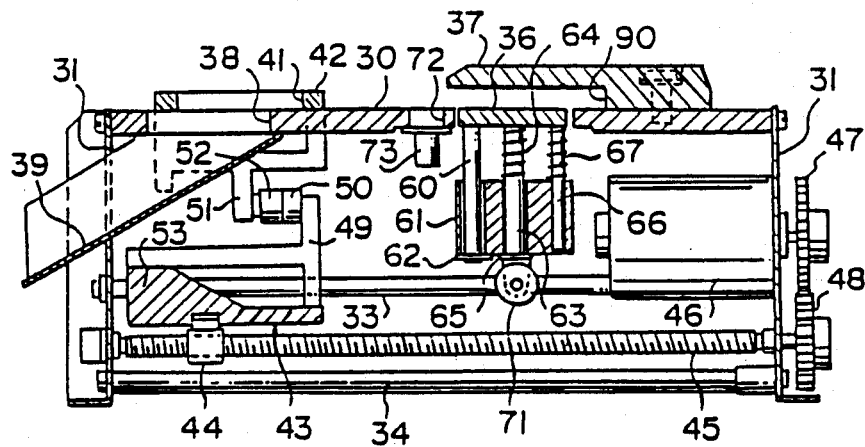

FIGS. 2, 3 and 4 show a mechanism disposed under the section at which the opening 12 is formed, and comprising a flat measuring device supporting base 30, a pair of side plates 31, 31 secured to opposite ends of the measuring device supporting base 30, and rods 32, 32, 33, 33, 34, 34 extending in parallel with the measuring device supporting base 30 for connecting the side plates 31, 31 with each other. A liquid applying section 30A is formed at the center of the measuring device supporting base 30, and the liquid applying section 30A is disposed between a potential difference measuring section 30B and a measuring device ejecting section 30C. The measuring device supporting base 30 is disposed inside the cover 11 so that the liquid applying section 30A is positioned accurately under the opening 12. The measuring device supporting base 30 is provided with a through hole 35 at the potential difference measuring section 30B, and a heating plate 36 movable in the vertical direction is disposed in the through hole 35. A slide retaining plate 37 is disposed at a position facing the heating plate 36 in spaced relation to the surface of the measuring device supporting base 30. At the measuring device ejecting section 30C, the measuring device supporting base 30 is provided with a slide ejection hole 38 which has a size larger than the slide 20 and which communicates with the ejection opening 13 of the cover 11 via a slanted passage 39 and an opening 40 in the side plate 31.

A measuring device holder 42 having a slide setting hole (through hole) 41 is disposed on the measuring device supporting base 30. Both ends of the measuring device holder 42 are slideably fitted to a pair of the rods 32, 32, and therefore the measuring device holder 42 is moveable in directions as indicated by the arrows A and B on the measuring device supporting base 30 to sequentially advance to the liquid applying section 30A, the potential difference measuring section 30B, and the measuring device ejecting section 30C. The slide retaining plate 37 is spaced from the surface of the measuring device supporting base 30 by a distance not less than the thickness of the measuring device holder 42 so that the measuring device holder 42 can move up to the position above the heating plate 36. On the other hand, a holder moving base 43 is disposed below the measuring device supporting base 30. Both ends of the holder moving base 43 are slideably fitted to a pair of the rods 33, 33, and therefore the holder moving base 43 is moveable in the directions as indicated by the arrows A and B. As shown in FIG. 4, a female thread member 44 is secured to the lower section of the holder moving base 43 and meshed with a drive screw (male thread) 45 disposed in parallel with the rods 33, 33. The drive screw 45 is rotated clockwise and counterclockwise by a motor 46, which is secured to the side plate 31, via gears 47 and 48 for moving the holder moving base 43 in the directions as indicated by the arrows A and B. Connection members 49, 49 upwardly projected are formed at opposite end sections of the holder moving base 43, and magnets 50, 50 are secured to the rear surfaces of the connection members 49, 49, i.e. the surfaces thereof facing the measuring device ejecting section 30C when the holder moving base 43 is present in the vicinity of the liquid applying section 30A. On the other hand, connection members 51, 51 projected downwardly are formed at opposite ends of the measuring device holder 42, and magnets 52, 52 facing the magnets 50, 50 are secured to the connection members 51, 51. The magnetic Polarity is adjusted so that the magnets 50, 50 adhere to the magnets 52, 52. Therefore, when the drive screw 45 is rotated to move the holder moving base 43 in the direction as indicated by the arrow A while the magnets 50, 50 adhere to the magnets 52, 52, the measuring device holder 42 is pulled by the holder moving base 43 and moved in the direction as indicated by the arrow A. On the other hand, when the holder moving base 43 is moved in the direction as indicated by the arrow B, the measuring device holder 42 is pushed by the holder moving base 43 and moved in the direction as indicated by the arrow B. A cam member 53 acting as a probe movement means is provided at the center of the holder moving base 43. The cam member 53 projects upwardly and has a cam surface 53a formed so that it is higher on the side of the measuring device ejecting section 30C and is lower on the side of the potential difference measuring section 30B.

Figure 5:
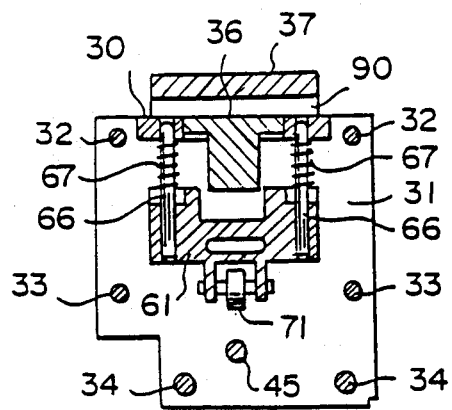
FIG. 5 is a sectional side view taken along line V—V of FIG. 3.
Figure 6:
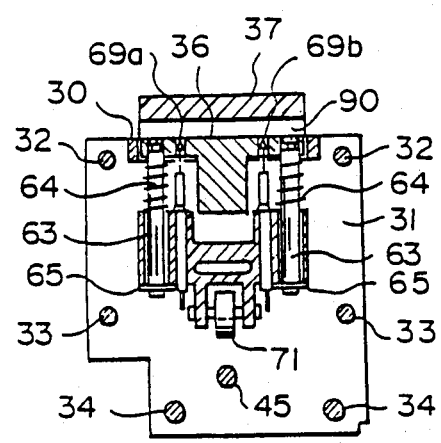
FIG. 6 is a sectional side view taken along line VI—VI of FIG. 3.

The configuration of the section around the heating plate 36 will hereinbelow be described by referring also to FIGS. 5 and 6 which are sectional views taken along line V—V and line VI—VI of FIG. 3. At the potential difference measuring section 30B, a pair of probe holder supporting rods 60, 60 are secured to the lower surface of the measuring device supporting base 30. The supporting rods 60, 60 are disposed with the heating plate 36 intervening therebetween, and a probe holder 61 is vertically slideably fitted to the supporting rods 60, 60. The probe holder 61 is stopped from below by washers 62, 62 secured to the lower ends of the supporting rods 60, 60. A pair of heating plate supporting rods 63, 63 are vertically slideably inserted through the probe holder 61, and the heating plate 36 is secured to the upper ends of the supporting rods 63, 63. Springs 64, 64 are disposed in the compressed form around the supporting rods 63, 63 between the heating plate 36 and the probe holder 61 for urging the heating plate 36 and the probe holder 61 to move away from each other. The probe holder 61 thus urged is stopped by washers 65, 65 secured to the lower ends of the heating plate supporting rods 63, 63. The lengths of the supporting rods 60, 60 and the supporting rods 63, 63 are adjusted so that the upper surface of the heating plate 36 is flush with the surface of the measuring device supporting base 30 when the lower surface of the probe holder 61 is stopped by the washers 65, 65 and the washers 62, 62. Also, lower ends of a pair of guide rods 66, 66 are secured to the probe holder 61. The guide rods 66, 66 are disposed to sandwich the heating plate 36 therebetween, and the upper ends of the guide rods 66, 66 are projectable upwardly of through holes 30d, 30d formed in the measuring device supporting base 30. Springs 67, 67 are disposed in the compressed form around the guide rods 66, 66 between the measuring device supporting base 30 and the probe holder 61. Therefore, when the probe holder 61 is pushed up from below, it resiliently moves up together with the heating plate 36 along the supporting rods 60, 60. In the case where the heating plate 36 is pushed from above at this time, the probe holder 61 is resiliently moved with respect to the heating plate 36.

Also, the probe holder 61 is provided with upwardly projecting probes 68a, 68b, 69a, 69b, 70a and 70b for measurement of differences in potential (by way of example, three pairs of the probes in this embodiment). The probes 68a, 68b, 69a, 69b, 70a and 70b are projectable upwardly of the heating plate 36 through notches or through holes formed in the heating plate 36. Specifically, when the heating plate 36 and the probe holder 61 are spaced apart from each other by the largest distance as shown in FIG. 4 by the effect of the springs 64, 64, the upper ends of the probes 68a, 68b, 69a, 69b, 70a and 70b are positioned inwardly of the heating plate 36. When the probe holder 61 is moved with respect to the heating plate 36 as mentioned above, the upper ends of the probes 68a, 68b, 69a, 69b, 70a and 70b are projected upwardly from the surface of the heating plate 36. Further, a roller 71 is disposed at the lower section of the probe holder 61 at the position facing the cam member 53 of the holder moving base 43. A through hole 72 is perforated through the measuring device supporting base 30 at a position between the liquid applying section 30A and the potential difference measuring section 30B, and a bar code sensor 73 is disposed under the through hole 72.

When measurement of ionic activity is carried out, the measuring device holder 42 is in the condition coupled with the holder moving base 43, the motor 46 is operated by being controlled by a known position sensor or a drive control circuit, and the measuring device holder 42 is positioned at the liquid applying section 30A. As mentioned above, in this condition, the measuring device holder 42 is positioned precisely under the opening 12 of the cover 11. Therefore, it is possible to insert the slide 20 into the slide setting hole 41 of the measuring device holder 42 via the opening 12.

Figure 7:
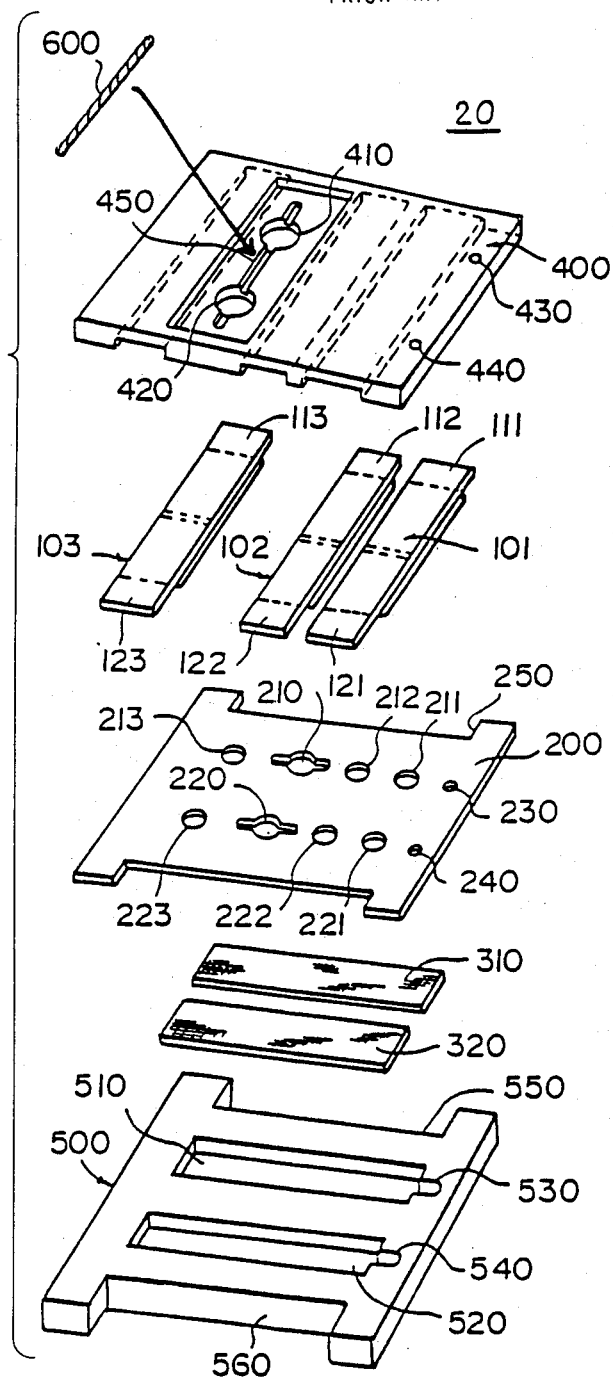
FIG. 7 is a perspective exploded view showing an example of the slide type ionic activity measuring device with which the analyzer is used.

The slide 20 may be of the type as described in Japanese Unexamined Patent Publication No. 58(1983)-211648, Japanese Patent Application Nos. 60(1985)-148564 and 60(1985)-180358, and Japanese Utility Model Application No. 60(1985)-204699. The configuration of the slide 20 will now be described briefly with reference to FIG. 7. The slide 20 comprises an upper frame half 400 and a lower frame half 500 formed of a plastic material. Between the upper frame half 400 and the lower frame half 500, there are housed an ion selective electrode pair 101 comprising ion selective electrodes 111 and 121 having ion selective layers of the same type on their surfaces and electrically isolated from each other, an ion selective electrode pair 102 comprising ion selective electrodes 112 and 122 having ion selective layers of the same type on their surfaces and electrically isolated from each other, an ion selective electrode pair 103 comprising ion selective electrodes 113 and 123 having ion selective layers of the same type on their surfaces and electrically isolated from each other, a water-impermeable member layer 200 having adhesive layers on both surfaces, and a pair of porous liquid distributing members 310 and 320 formed of cotton and regenerated cellulose fiber nonwoven fabrics having continuous pores.

The upper frame half 400 is provided with a pair of liquid feed holes 410 and 420, and a recess 450 extending across the liquid feed holes 410 and 420. A porous bridge 600 formed of polyethylene terephthalate fibers or the like is housed and secured in the recess 450. The depth of the recess 450 is set to such a value that the bridge 600 does not project from the upper surface of the upper frame half 400.

The water-impermeable member layer 200 disposed below the upper frame half 400 with the ion selective electrode pairs 101, 102 and 103 intervening therebetween is provided with through holes (liquid descent passages) 210 and 220 matched with the liquid feed holes 410 and 420, and through holes (liquid ascent passages) 211, 212, 213, 221, 222 and 223 respectively matched with portions of ion selective layer regions of the ion selective electrodes 111, 112, 113, 121, 122 and 123. Under the water-impermeable member layer 200, the porous liquid distributing member 310 is disposed to match with the through holes 210, 211, 212 and 213, and the porous liquid distributing member 320 is disposed to match with the through holes 220, 221, 222 and 223. The lower frame half 500 is provided with recesses (horizontal liquid passages) 510 and 520 having shapes capable of housing therein the porous liquid distributing members 310 and 320. Also, the upper frame half 400, the water-impermeable member layer 200, and the lower frame half 500 are respectively provided with a pair of through holes (air discharging holes) 430 and 440, a pair of through holes 230 and 240, and a pair of through holes 530 and 540, which constitute air discharging holes extending through the whole slide 20. The ion selective electrode pairs 101, 102, and 103 are disposed with their ion selective layers facing down, and terminal sections of these ion selective electrode pairs are exposed at the lower surface of the slide 20 from a pair of cutaway sections 250 and 260 of the water-impermeable member layer 200, and a pair of cutaway sections 550 and 560 of the lower frame half 500.

In this slide 20, the ion selective electrode pairs 101, 102, and 103 are respectively provided with the ion selective layers selectively responding to, for example, $Cl^-$, $K^+$, and $Na^+$ ions. A reference solution containing these ions whose ionic activity values are known is applied to the liquid feed hole 410, and a sample solution whose ionic activity values are unknown is applied to the liquid feed hole 420. The applied reference solution permeates through the porous liquid distributing member 310 via the liquid descent passage 210, and then passes through the liquid ascent passages 211, 212 and 213 to the ion selective layers of the ion selective electrodes 111, 112 and 113. The applied sample solution permeates through the porous liquid distributing member 320 via the liquid descent passage 220, and then passes through the liquid ascent passages 221, 222 and 223 to the ion selective layers of the ion selective electrodes 121, 122 and 123. Also, the reference solution and the sample solution come into contact with each other near the center of the bridge 600, thereby giving rise to electrical conduction therebetween. As a result, differences in potential corresponding to the differences in ionic activity of the $Cl^-$, $K^+$, and $Na^+$ ions between the reference solution and the sample solution are given rise to between the ion selective electrodes 111 and 121, between the ion selective electrodes 112 and 122, and between the ion selective electrodes 113 and 123. Accordingly, when potential measuring probes are inserted from below the cutaway sections 550 and 560 until they contact the terminal sections of the ion selective electrodes and the difference in potential across each ion selective electrode pair is measured, it is possible to measure the ionic activity of each ion in the sample solution.

The slide 20 is inserted into the slide setting hole 41 with the upper frame half 400 facing up, and the reference solution and the sample solution are applied respectively to the liquid feed holes 410 and 420 by use of, for example, a dual pipette. When the start pushbutton 14 as shown in FIG. 1 is depressed, the motor 46 is operated, and the holder moving base 43 is moved in the direction as indicated by the arrow A. The measuring device holder 42 is also moved towards the potential difference measuring section 30B by being pulled by the holder moving base 43, and comes into contact with a stopper 90. Thus the slide 20 held on the measuring device holder 42 is stopped at a predetermined position facing the heating plate 36. The motor 46 continues to operate, and the holder moving base 43 is further moved by a predetermined distance. At this time, since movement of the measuring device holder 42 is restrained by the stopper 90, the magnets 50, 50 are separated from the magnets 52, 52, and the holder moving base 43 is moved alone as mentioned above. When the holder moving base 43 is thus moved, the cam surface 53a of the cam member 53 comes into contact with the roller 71 of the probe holder 61, and pushes the probe holder 61 up. As a result, the heating plate 36 is pushed up as mentioned above, and pushes up and fixes the slide 20, which is held on the measuring device holder 42, to the slide retaining plate 37. At this time, as the probe holder 61 is moved up, the guide rods 66, 66 are projected upwardly from the measuring device supporting base 30, inserted into guide holes 91, 91 of the measuring device holder 42, and adjust the position of the measuring device holder 42, and consequently the position of the slide 20, at a predetermined position. When the slide 20 has been pushed against the slide retaining plate 37 in this manner, upward movement of the heating plate 36 is restrained. The probe holder 61 is further pushed up by a predetermined distance, and the probes 68a, 68b, 69a, 69b, 70a and 70b are thereby projected upwardly of the surface of the heating plate 36. The probes 68a and 68b thus projected up are inserted into the cutaway sections 550 and 560 of the slide 20 from below, and come into contact with the ion selective electrodes 111 and 121. Also, the probes 69a and 69b are inserted into the cutaway sections 550 and 560 from below, and come into contact with the ion selective electrodes 112 and 122. In the same manner, the probes 70a and 70b are inserted into the cutaway sections 550 and 560 from below, and contact the ion selective electrodes 113 and 123.

In this condition, the motor 46 is stopped, and then the slide 20 is heated to a predetermined temperature by the heating plate 36. After a predetermined time has elapsed, differences in potential across the ion selective electrode pair 101, across the ion selective electrode pair 102, and across the ion selective electrode pair 103 are measured by use of known potential difference measuring circuits (not shown) connected to the probes 68a, 68b, 69a, 69b, 70a and 70b. As mentioned above, ionic activity values of the $Cl^-$, $K^+$ and $Na^+$ ions are measured by measuring the differences in potential. As shown in FIG. 1, the ionic activity values thus measured are indicated on the displaying section 15, or recorded on recording paper 17 at the recording section 16. The bar code of the slide 20 subjected to the measurement of differences in potential is read out by the bar code sensor 73, and the ionic activity values are displayed or recorded together with the identification code of the slide 20.

When measurement of the differences in potential is finished, the motor 46 is rotated in the reverse direction to move the holder moving base 43 in the direction as indicated by the arrow B. Thus the cam member 53 is gradually moved away from the roller 71 of the probe holder 61, and the probe holder 61 is moved down. Therefore, the probes 68a, 68b, 69a, 69b, 70a and 70b are first separated from the slide 20, the guide rods 66, 66 are moved down from the guide holes 91, 91 of the measuring device holder 42, and the heating plate 36 is moved down to the position where its surface is matched with the surface of the measuring device supporting base 30. Since the motor 46 continues to be operated and the holder moving base 43 continues to be moved, the connection members 49, 49 of the holder moving base 43 push the connection members 51, 51 via the magnets 50, 50 and the magnets 52, 52, and the measuring device holder 42 is moved in the direction as indicated by the arrow B. Accordingly, the slide 20 for which the potential difference measurement has been finished is sent by the measuring device holder 42 from the potential difference measuring section 30B t the liquid applying section 30A. The motor 46 is operated until the measuring device holder 42 comes to the position above the measuring device ejecting section 30C. When the measuring device holder 42 comes to the position above the measuring device ejecting section 30C, the slide 20 held on the measuring device holder 42 is allowed to fall into the slide ejection hole 38. The slide 20 is ejected from the ejection opening 13 via the passage 39. Then, the motor 46 is rotated reversely to send the measuring device holder 42 to the liquid applying section 30A, and the measuring device holder 42 is stopped at the liquid applying section 30A and waits for the next applying operation.

Embodiments of the simple inspection device for an analyzer for ionic activity measurement in accordance with the present invention will be described hereinbelow.

FIG. 8 shows an embodiment of the first simple inspection device for an analyzer for ionic activity measurement in accordance with the present invention. As shown in FIG. 8, a simple inspection device 1 comprises an upper mount 2 and a lower mount 3 constituting a supporting member, and a metal plate 4 secured between the upper mount 2 and the lower mount 3. The upper mount 2 and the lower mount 3 have outer dimensions approximately equal to the outer dimensions of the upper frame half 400 and the lower frame half 500 of the slide 20, and are formed of, for example, a plastic material. The upper frame half 400 and the lower frame half 500 may be utilized respectively as the upper mount 2 and the lower mount 3. On the other hand, the metal plate 4 is formed of a material which is corrosion resistant and highly durable, for example, stainless steel. In this embodiment, the metal plate 4 has length and width dimensions approximately equal to the length and width dimensions of the upper mount 2 and the lower mount 3. Also, the lower mount 3 is provided with through holes 3a, 3b, 3c, 3d, 3e and 3f at positions respectively corresponding to the through holes 211, 212, 213, 221, 222 and 223 of the water-impermeable member layer 200 of the slide 20.

In the course of inspecting whether the analyzer 10 is or is not operating correctly, the simple inspection device 1 having the aforesaid configuration is inserted into the slide setting hole 41 instead of the slide 20. In this case, since the upper mount 2 and the lower mount 3 have the aforesaid outer dimensions, the simple inspection device 1 is snuggly accommodated in the slide setting hole 41. At this time, the simple inspection device 1 is set in the slide setting hole 41 with the upper mount 2 facing up. Then, the start pushbutton 14 is depressed to move the holder moving base 43 so that it can up the probe holder 61 in the same manner as in the course of measurement of ionic activity. As a result, the probes 68a, 68b, 69a, 69b, 70a and 70b are projected upwardly. The probes 68a and 68b pass through the through holes 3a and 3d of the lower mount 3, the probes 69a and 69b pass through the through holes 3b and 3e of the lower mount 3, and the probes 70a and 70b pass through the through holes 3c and 3f of the lower mount 3. Thus the probes 68a, 68b, 69a, 69b, 70a and 70b contact the metal plate 4. Therefore, the probes are short-circuited across the probes 68a and 68b across the probes 69a and 69b, and across the probes 70a and 70b.

In the case where the electric circuit of the analyzer is normal, the difference in potential between each pair of the probes is equal to zero upon short-circuiting across the probes as mentioned above. The zero value of the difference in potential is indicated on the displaying section 15, and the inspector can confirm that the analyzer 10 is capable of operating normally based on the displayed value.

On the other hand, in the case where the analyzer is operating abnormally, for example, in the case where a contact failure portion, a broken wire, a defective relay, a defective amplifier or the like is present in the electric circuit of the analyzer, the difference in potential between the probes does not become zero upon short-circuiting thereof. Therefore, the inspector can confirm that a problem has arisen with the analyzer 10 based on the value indicated on the displaying section 15.

Another embodiment of the first simple inspection device for an analyzer for ionic activity measurement in accordance with the present invention will now be described with reference to FIG. 9. In FIG. 9, similar elements are numbered with the same reference numerals with respect to FIG. 8. A simple inspection device 5 shown in FIG. 9 comprises metal plates 6, 7 and 8 disposed independently of each other, instead of the large metal plate 4 shown in FIG. 8. The metal plates 6, 7 and 8 are secured at positions corresponding respectively to the ion selective electrode pairs 101, 102 and 103 of the slide 20. The simple inspection device 5 having the aforesaid configuration is used for inspection of the analyzer 10 in the same manner as the simple inspection device 1 shown in FIG. 8. With the simple inspection device 5, the normal or abnormal condition of the analyzer 10 can be confirmed in the same manner as the simple inspection device 1 shown in FIG. 8. With the simple inspection device 5 wherein the metal plates 6, 7 and 8 for respectively short-circuiting across the probes 68a and 68b, across the probes 69a and 69b, and across the probes 70a and 70b are disposed independently of each other and electrically isolated from each other, incorrect wire connections among the potential difference measuring probes (68a, 68b, 69a, 69b, 70a, and 70b) and relays, and contact failures and broken wires in the three circuit lines can be confirmed for each of the circuit lines.

The metal plates 6, 7 and 8 may be formed of stainless steel or the like as mentioned above, or may be formed of copper alloy plates or the like having the surface plated with tin or gold in order to increase the anticorrosion effects and to improve the electrical contact condition. This modification applies also to the metal plate 4 shown in FIG. 8.

An embodiment of the second simple inspection device for an analyzer for ionic activity measurement in accordance with the present invention will hereinbelow be described with reference to FIG. 10. A simple inspection device 1' shown in FIG. 10 comprises a metal plate 4A facing the through holes 3a, 3b and 3c, and a metal plate 4B facing the through holes 3d, 3e and 3f. The metal plates 4A and 4B may be formed of stainless steel or the like as mentioned above, or may be formed of copper alloy plates having the surface plated with gold or the like. The metal plate 4A and 4B are associated with each other by a thin chip resistor 4C i.e. a resistor in the form of a chip.

At the time a reference solution and a sample solution are applied in drops to the slide 20 and liquid junction is achieved between the reference solution and the sample solution near the middle of the bridge 600, the electrical resistance across the ion selective electrodes 111 and 121 for the Cl$^-$ ion is approximately 100kΩ, for example. Also, at this time, the electrical resistance across the ion selective electrodes 112 and 122 for the K$^+$ ion is approximately 10MΩ, and the electrical resistance across the ion selective electrodes 113 and 123 for the Na$^+$ ion is approximately 1MΩ. Accordingly, as the chip resistor 4C, a resistor of approximately 1MΩ, which value is an intermediate value among the aforesaid three resistance values, is utilized.

Also, with the simple inspection device 1', an abnormality of the analyzer 10 can be found in the same manner as with the simple inspection device 1 or the simple inspection device 5.

As mentioned above, the electrical resistance across the metal plates 4A and 4B is adjusted to a value close to the electrical resistance values produced across the ion selective electrodes 111 and 121, across the ion selective electrodes 112 and 122, and across the ion selective electrodes 113 and 123 at the time of measurement of ionic activity. In the case where a ground failure arises with the electric circuit or the main body of the analyzer 10, the electric circuit is adversely affected by noise, and the potential value indicated on the displaying section 15 fluctuates unstably to the "+" (plus) side or to the "−" (minus) side. Therefore, the ground failure can be found by investigating the fluctuation of the potential value indicated on the displaying section 15.

Another embodiment of the second simple inspection device for an analyzer for ionic activity measurement in accordance with the present invention will hereinbelow be described with reference to FIG. 11. A simple inspection device 5' shown in FIG. 11 comprises metal plates 6A and 6B respectively facing the through holes 3a and 3d, metal plates 7A and 7B respectively facing the through holes 3b and 3e, and metal plates 8A and 8B respectively facing the through holes 3c and 3f. The metal plates 6A and 6B are associated with each other by a chip resistor 6C, the metal plates 7A and 7B are associated with each other by a chip resistor 7C, and the metal plates 8A and 8B are associated with each other by a chip resistor 8C. The electrical resistance values of the chip resistors 6C, 7C and 8C are adjusted respectively to approximately 100kΩ, 10MΩ and 1MΩ to match the electrical resistance values produced across the ion selective electrodes 111 and 121, across the ion selective electrodes 112 and 122, and across the ion selective electrodes 113 and 123 at the time of measurement of ionic activity.

With the simple inspection device 5' wherein the electrical resistance values across the metal plates 6A and 6B, across the metal plates 7A and 7B, and across the metal plates 8A and 8B are adjusted to the levels as mentioned above, the level of the effects of noise which the three circuit lines having the probes 68a and 68b, the probes 69a and 69b, and the probes 70a and 70b as the detection terminals receive in the course of inspection of the analyzer is close to the extent of effects of noise arising in the course of measurement of ionic activity. Accordingly, with the simple inspection device 5', inspection of the analyzer can be carried out more accurately.

Though the analyzer 10 constituted such that the slide 20 is automatically sent to and ejected from the potential difference measuring section is taken as an example, the simple inspection device for an analyzer for ionic activity measurement in accordance with the present invention is not limited to the use for the analyzer of this type, and is applicable also to an analyzer so constituted that the slide 20 is manually sent to and ejected from the potential difference measuring section.

We claim:

1. A method for testing operability of an analyzer for ionic activity measurement by use of an inspection device, the analyzer having at least two potential difference measuring probes, the inspection device having first and second electrically non-conductive members supporting at least one electrically conductive member therebetween, one of the non-conductive members having apertures formed therein, the method comprising the steps of:

(i) positioning the inspection device so as to receive the probes through the apertures to electrically connect the probes; and (ii) determining an electric potential difference between the probes.

2. An analyzer for ionic activity measurement and an inspection device for testing the functions of the analyzer, said analyzer comprising:

an ionic activity measuring device having at least one ion selective electrode pair for generating an electric potential corresponding to ionic activity of a predetermined ion, and a porous bridge connecting the electrodes of said ion selective electrode pair with each other;

a measurement device holder removably supporting said ionic activity measuring device; and a plurality of potential difference measuring probes mounted for movement towards and away from respective electrodes of said ionic activity measuring device supported by said measuring device holder, to thereby measure a difference in potential between said electrodes, wherein said inspection device is mountable on said holder in lieu of said ionic activity measuring device, and said inspection device comprises:

electrically non-conductive supporting means for being removably supported by said holder; and an electrically conductive member supported on said supporting means for contacting said potential difference measuring probes to short-circuit said probes to thereby indicate one of operability and inoperability of said analyzer, said supporting means being formed with access means for allowing said electrically conductive member to be contacted by said probes.

3. An analyzer and an inspection device as defined in claim 2, wherein said supporting means is composed of an upper mount and a lower mount for supporting said electrically conductive member therebetween, and wherein said access means comprises through-holes formed in one of said mounts and aligned with respective probes for permitting contact between said probes and said electrically conductive member after probe penetration through said through-holes.

4. An analyzer and an inspection device as defined in claim 2, wherein said electrically conductive member is composed of a metal having a surface plated with tin or gold.

5. An analyzer and an inspection device as defined in claim 2, wherein said supporting means has outer dimensions which correspond to outer dimensions of said measurement device holder.

* * * * *